United States Patent
Brosa

Patent Number: 5,772,670
Date of Patent: Jun. 30, 1998

[54] FORCEPS FOR THE SURGICAL INTRODUCTION OF CATHETERS AND THE LIKE

[76] Inventor: Ramón Bofill Brosa, Passatge Jardiner, 8, 08190 Valldoreix, Spain

[21] Appl. No.: 878,205

[22] Filed: Jun. 18, 1997

[51] Int. Cl.[6] .................................................. A61B 17/28
[52] U.S. Cl. .......................... 606/108; 606/207; 606/205
[58] Field of Search ................................. 606/205–209, 606/108, 106

[56] References Cited

U.S. PATENT DOCUMENTS 3,844,274  10/1974  Nordstrom .
4,484,911  11/1984  Berlin et al. .
4,608,982   9/1986  Pollard .

FOREIGN PATENT DOCUMENTS

WO 9108709  6/1991  Spain .

*Primary Examiner*—Michael Buiz
*Assistant Examiner*—David O. Reip
*Attorney, Agent, or Firm*—Cushman Darby & Cushman IP Group of Pillsbury Madison & Sutro LLP

[57] ABSTRACT

The forceps are characterized in that their extreme appendixes are provided with means for the soft holding and for the guiding of the tubular element to be introduced into an opening provided in the body during a surgical operation and, preferably the appendixes of the forceps have respective grooves opposite to each other and forming a channel for guiding a flexible tubular element or the like, fixed and guided by the forceps appendixes, the forceps being further characterized by side openings in the appendixes of the forceps for the purpose of introducing the tubular element fixed and guided by said forceps.

2 Claims, 4 Drawing Sheets

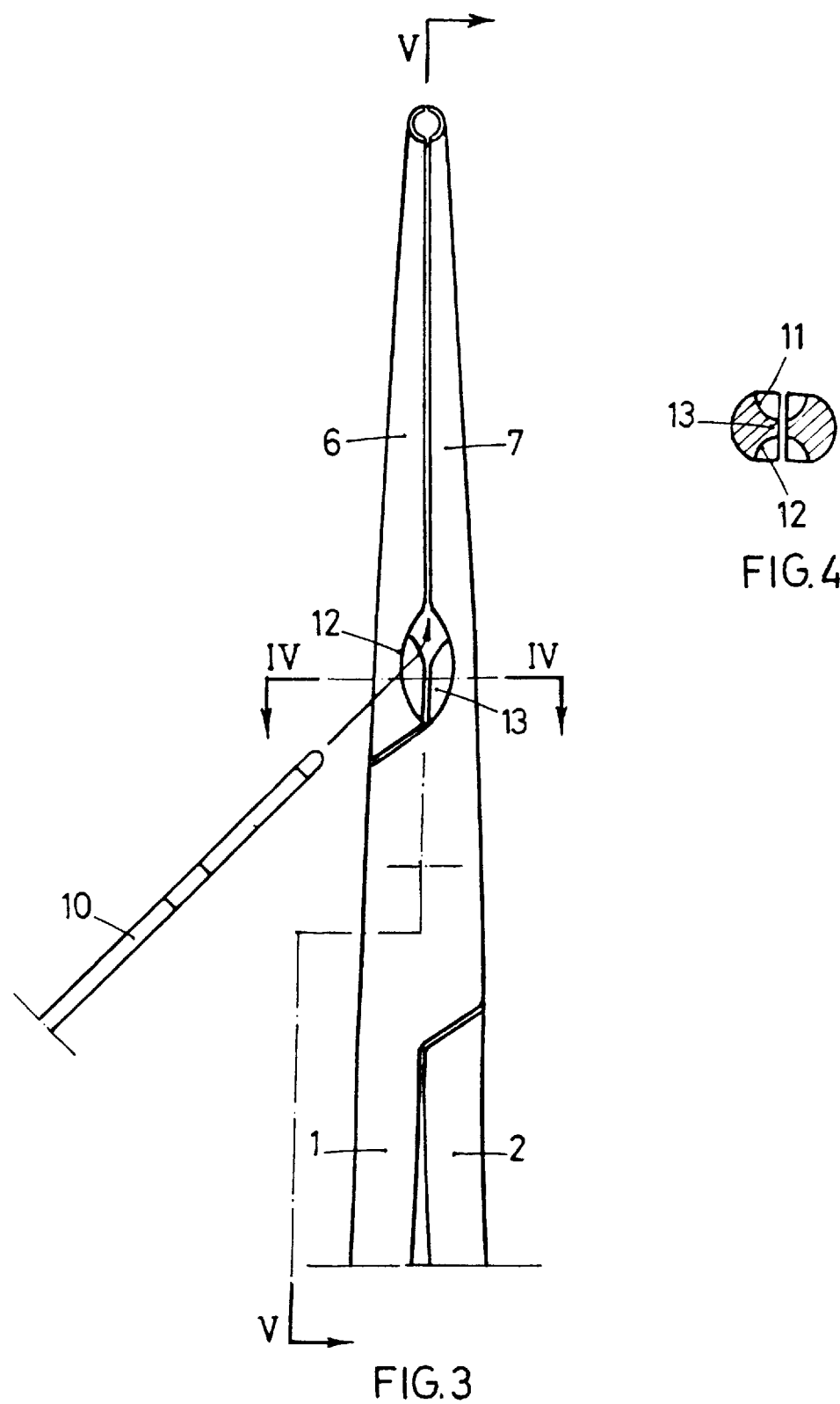

FORCEPS FOR THE SURGICAL INTRODUCTION OF CATHETERS AND THE LIKE

This is a Continuation of International Appln. No. PCT/ES96/00194 filed Oct. 17, 1996 which designated the U.S.

DESCRIPTION

The present invention relates to a new device for the surgical introduction of catheters and other similar surgical devices such as probes, guides, endotracheal tubes, optical fibers for viewing and illumination, and the like, the said device having significant features of novelty and inventive step compared to the prior art.

The forceps according to the present invention has been originally designed and manufactured for use in vascular surgery and, more specifically, to facilitate the introduction of spherical probes (Fogarty) into the lumen of a blood vessel, through its point of emergence from the corresponding principal trunk. Subsequently it has been considered convenient to use the forceps in other medical and surgical specialties such as thoracic surgery, cardiac surgery, gastrology, urology, ear nose and throat surgery, anaesthesia, etc., in cases requiring a similar use of this instrument in order to introduce all types of probes, catheter guides, optical fibers and tubes, the instrument being suitably adapted in each particular case.

The forceps according to the present invention are characterised by completely original features not known in the relevant field of application, which enable the forceps to achieve their objectives for which reason it enjoys remarkable features of novelty and inventive step.

The tubular element is preferably lightly gripped by the jaws of the forceps so as to enable the said tubular element to be simply placed in the desired opening or cavity and released easily therein by an unclamping action, namely by opening the end jaws of the forceps so that the tubular element remains in position and the forceps can easily be removed, leaving the tubular element secured in a reliable and simple manner in the desired position.

The gripping and guidance of the tubular element may be effected in many different ways, in which connection it should be noted in any case that the combination of the two end jaws of the forceps provide means for lightly gripping and guiding the aforementioned tubular element. Thus, for example, in a preferred embodiment each of the jaws of the forceps has a longitudinal groove so that when both jaws adjoin one another in the closed position, prior to the use of the forceps, the longitudinal grooves of the two jaws coincide forming a channel intended to receive the tubular element. Nevertheless, other embodiments are possible that meet the basic objectives of the present invention as regards the gripping and guidance of a tubular element by the ends or jaws of forceps or the like. For example, it would be possible to design the longitudinal groove so as to have an irregular shape, being larger in one of the jaws of the forceps than in the other, or for the longitudinal groove to be contained completely in one of the jaws of the forceps, the other jaw being in longitudinal contact with the said tubular element so as to grip the latter. Likewise, it is also possible for one of the jaws or ends of the forceps to have an asymmetric longitudinal groove so as to complement the action of the other jaw.

In order to facilitate the introduction of the tubular element into the forceps as well as the withdrawal of the forceps once the tubular element has been introduced, the present invention provides that, in the case where the longitudinal grooves of the jaws of the forceps are formed in the internal part of the said jaws, lateral openings are provided in the latter so as to permit the lateral introduction of the tubular element as far as the guide channel defined by the grooves of the jaws, at the same time facilitating the removal of the forceps once the surgical intervention has been effected.

In a specific case the device has an external shape and configuration similar to Rumel or Harrington type surgical dissection forceps, having two extended and interconnected elements with an articulation joint at their intersection so that the device can act like a pair of scissors. In the intersection region the component elements of the forceps have a flatter shape and one of them engages the other via a groove to improve the gripping action. The central or intermediate part of both elements extends in opposite directions, symmetry being preserved with respect to the mid-line.

In this embodiment, the end jaws of each of the elements of the forceps have an extended and substantially cylindrical shape forming an acute angle with the central part. Both segments are joined distally with respect to the point of intersection at two bows or rings to accommodate the thumb and fingers actuating the forceps. The forceps have in the region adjacent to the aforementioned bows a conventional toothed locking device normally employed in dissection or vascular surgery forceps.

At the opposite end, the two component elements of the forceps have a semi-tubular and curved shape so that when they engage and fit together they form a cylindrical housing with an angle of rotation of approximately 90°.

The proximal part of each of these semi-tubular segments, also with respect to the central part, comprises two semi-circular recesses each facing the aforementioned plane, that start respectively from the surface of each of these segments of the forceps and extend to the deep part of the two channels that converge in the form of an inverted Y in the main semi-channel. These recesses are shaped as orifices that likewise face the plane of the piece when the latter are in the closed position, forming a tubular space. The desired linear object may be introduced through such orifices. In the case of a catheter for example, making a small angle with respect to the longitudinal axis or mid-line of the forceps, when it is inserted through either of the said orifices and the corresponding small channel it can reach the main channel by means of a slight forward pressure. Finally, following the same direction of movement, the catheter bends laterally at the point where the channel also bends, and ends outside the forceps. Following this the catheter can be guided to the desired point for its installation.

It should be noted that the combination of a mandrel with a sharp tip in the manner of a Seldinger needle enables the forceps to be used percutaneously.

As regards the construction of the forceps, stainless steel or lighter materials such as titanium and the like, including plastics, may be used for this purpose.

It is also possible to replace a scissors-type mechanism by another system that separates the segments in a parallel form.

It is also possible to design and produce modifications in which the tubular part has Larger angles for introducing materials that are less flexible on account of their size.

The orifices for introducing the catheter may be constructed so that they are surrounded on the outside by a lobed or flap-type structure.

The device according to the present invention has, inter alia, the following advantages:

The use of the device in the form of forceps permits remote access between the point where the tip of the probe or catheter is introduced and the surgeon's hand, this feature being very advantageous in anatomical spaces such as the groin of obese patients, in which the common femoral artery and the emergence of the deep femoral artery are difficult to cathetferise. On completing this procedure the probe can be fully released by opening the forceps. In this case the distal end of the probe can remain in the position in which it was placed.

It is also easier to introduce a catheter or similar element into emerging ducts, channels or tubular structures that form an angle that complicates the introduction of such surgical devices, which despite their flexibility nevertheless exhibit some resistance to bending.

The curvature of the mid part of the channelled segment facilitates the advance of the tip of the catheter or probe in a specific direction relative to the proximal segment through which it is introduced.

The introduction of surgical devices through opposite orifices enables the same forceps to be used in different, including opposite directions, thereby enabling the forceps to be used by left-handed persons.

Obviously, the necessary care must be taken when opening the forceps to prevent damage to surrounding structures.

A specific embodiment of the device for the surgical introduction of catheters and the like in accordance with the present invention Ls described hereinafter with the aid of the following drawings, in which:

FIG. 1 is a plan view of the complete forceps, showing the arrangement of a catheter tube or the like.

FIG. 3 is another detail of the end of the forceps showing the relative position of the end of the tubular element with respect to the forceps.

FIG. 4 is a transverse section of the device through the indicated sectional plane.

Figure 1:
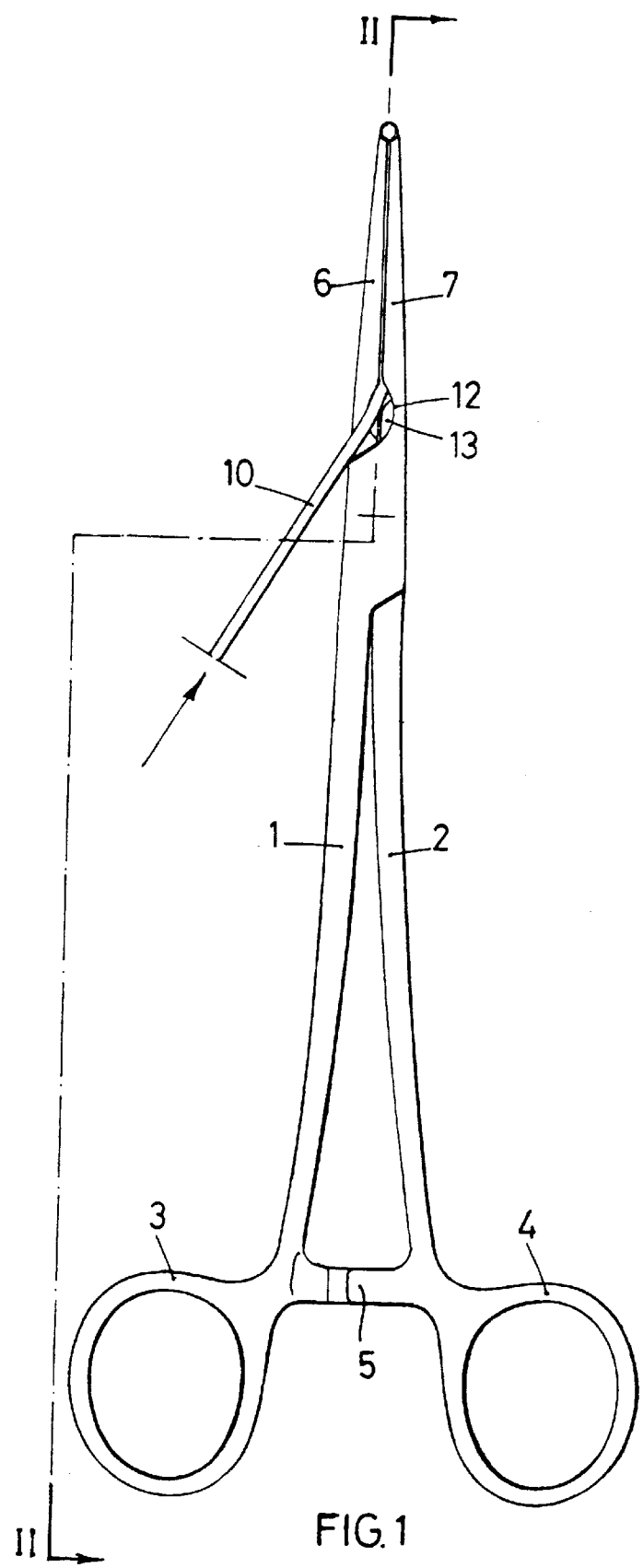
Figure 2:
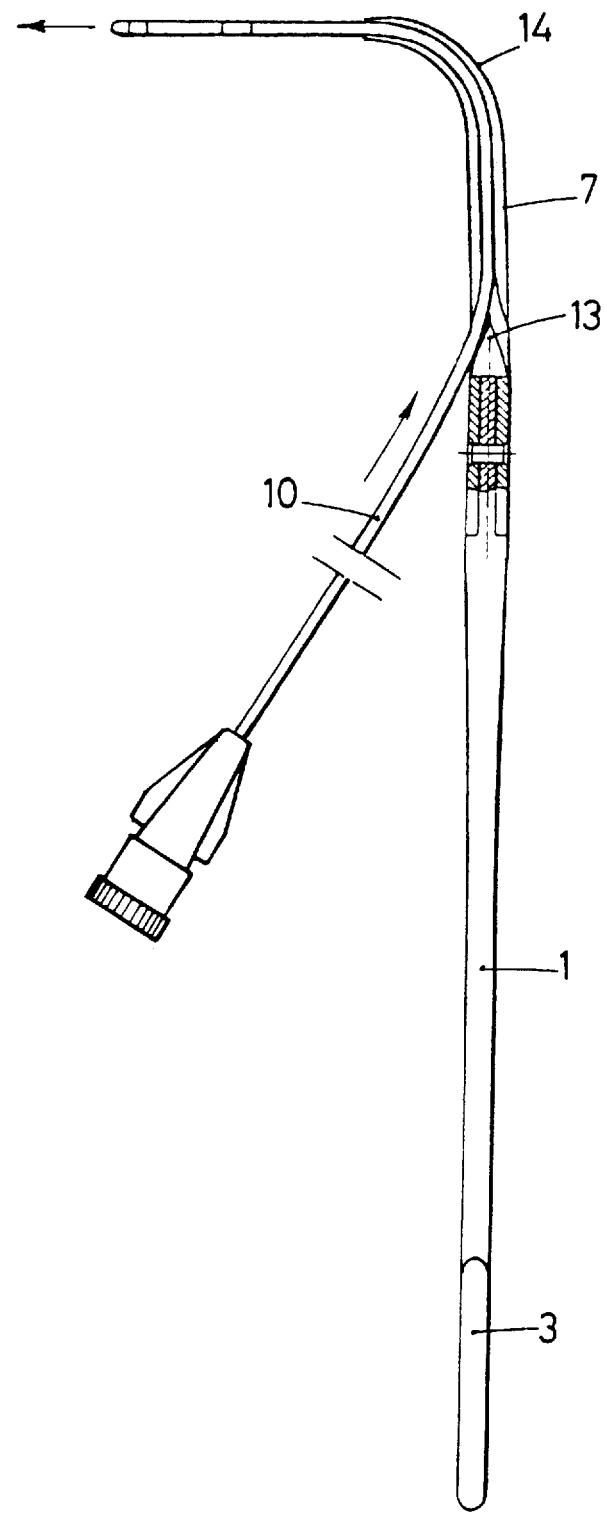
FIG. 2 shows in detail the introduction of the tube into the forceps.

As shown in the drawings, the device according to the present invention comprises two conventional type shanks 1 and 2 with manipulation bows 3 and 4 for accommodating the thumb and fingers, and optionally a ratchet-type connecting member 5. The elements 1 and 2 are articulatedly connected to one another by means of a conventional transverse joint and include in their front part the working jaws 6 and 7 which have at their end a curved structure forming an angle of approximately 90°, as shown in FIG. 2, and constituting an end region 14 aligned roughly perpendicular to the plane of the component elements of the forceps.

Figure 5:
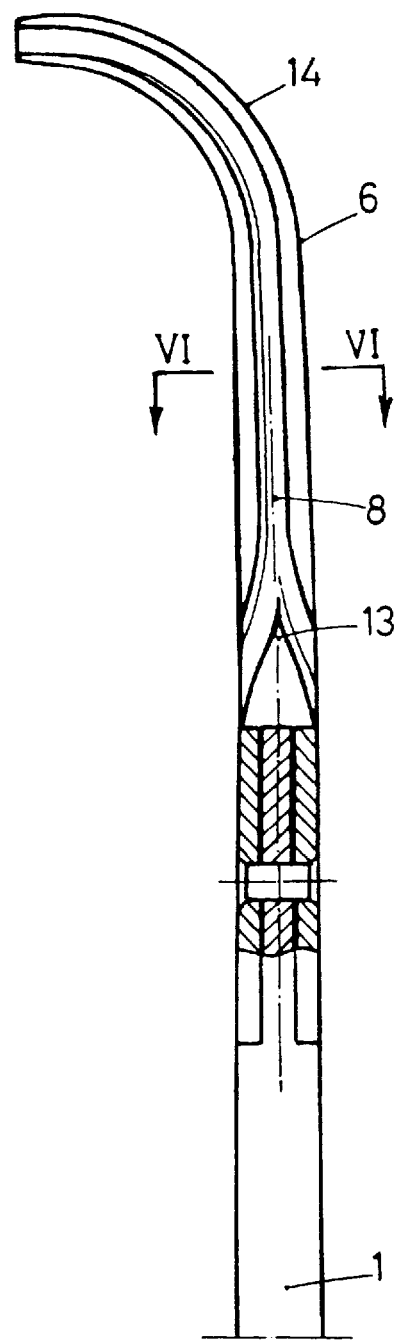
FIGS. 5 and 6 are respectively longitudinal and transverse sections of the device in the part corresponding to the curved end.
Figure 6:
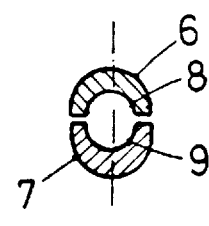

The interior of the working jaws 6 and 7 includes a longitudinal channel such as can be seen in FIG. 6, which shows the said jaws 6 and 7, in which the substantially semi-circular channels 8 and 9 can be seen in the interior. The arrangement is such that when the two jaws 6 and 7 engage in the closed position, as illustrated in FIG. 6, a practically cylindrical channel is formed that is intended to receive and guide a probe, catheter duct, etc., as indicated by the reference numeral 10. Each of the said jaws 6 and 7 has at its start lateral recesses such as 11 and 12 that communicate with inverted Y-shaped ends 13, FIG. 5, of the internal channels 8 and 9, thereby providing an arrangement to facilitate the introduction of the tubular element of the probe, catheter, etc., through either of the two sides of the aforementioned device, which represents a specific case of the present invention.

Although the preceding description refers to a specific embodiment of forceps according to the present invention, the said embodiment is not intended to restrict in any way the scope of the present invention, it being understood that the essential feature of the invention is that the end jaws of the forceps have means for gripping and guiding an elongated tubular element of the type described in the preceding paragraph, or also of the type comprising a catheter or the like, in such a way that the jaws of the forceps enable the said tubular element to be simultaneously gripped and guided as far as its point of introduction into the corresponding orifice or lumen of a blood vessel or other desired part of the human body.

As will be understood, the device according to the present invention for the surgical introduction of catheters, probes, etc. includes notably innovative features that in particular facilitate the work of the user or surgeon, especially in cases involving difficult manipulations.

What is claimed is:

1. Forceps for the surgical introduction of a flexible tubular element, comprising: first and second elongate elements, each of said elongate elements having at one end an opening for insertion of a finger and at an opposite end a curved jaw member having a semi-cylindrically shaped groove along a length of said jaw member, said elongate elements being pivotally connected at a pivot point and being configured such that, in a closed position, said grooves in said jaw members are opposed and define a tubular channel for gripping and guiding said flexible tubular element, said forceps further comprising, in said closed position, substantially elliptically-shaped orifices on opposing sides of said forceps and adjacent said pivot point, said orifices communicating with said grooves and providing access for insertion of said flexible tubular element into and through said tubular channel from either side of said forceps.

2. Forceps as defined in claim 1 wherein said jaw members are curved approximately 90 degrees.

* * * * *

UNITED STATES PATENT AND TRADEMARK OFFICE
CERTIFICATE OF CORRECTION

PATENT NO. : 5,772,670

DATED : June 30, 1998

INVENTOR(S) : BOFILL BROSA

It is certified that error appears in the above-identified patent and that said Letters Patent is hereby corrected as shown below:

On the title page,
Please add:    --Related U. S. Application Data

Item [63]   Continuation of international application number
               PCT/ES96/00194  filed Oct. 17, 1996--

Signed and Sealed this

Twenty-fifth Day of May, 1999

Attest:

Q. TODD DICKINSON

*Attesting Officer*      *Acting Commissioner of Patents and Trademarks*